US008496922B2

(12) United States Patent
Bogdanov

(10) Patent No.: US 8,496,922 B2
(45) Date of Patent: Jul. 30, 2013

(54) **PLANKTON STRAIN ALGAE *PARACHLORELLA NUREKIS* 1904 *KIEG* AND HIS USE TO EXTERMINATE CYANOBACTERIA, BACTERIA AND FUNGI**

(75) Inventor: Nikolay Bogdanov, Pěnzenská oblas (RU)

(73) Assignee: Key Group Holding, S.R.O., Prague (CZ)

( * ) Notice: Subject to any disclaimer, the term of this patent is extended or adjusted under 35 U.S.C. 154(b) by 0 days.

(21) Appl. No.: 13/508,486

(22) PCT Filed: Mar. 30, 2010

(86) PCT No.: PCT/CZ2010/000035
§ 371 (c)(1),
(2), (4) Date: May 7, 2010

(87) PCT Pub. No.: WO2011/107061
PCT Pub. Date: Sep. 9, 2010

(65) Prior Publication Data
US 2012/0225036 A1    Sep. 6, 2012

(30) Foreign Application Priority Data

Mar. 4, 2010    (CZ) .................................. 2010-57

(51) Int. Cl.
*C12N 1/12* (2006.01)
*A01P 1/00* (2006.01)
*A01P 3/00* (2006.01)
*C02F 3/32* (2006.01)
*A01N 65/03* (2009.01)

(52) U.S. Cl.
USPC .................. 424/93.1; 210/602; 435/257.1

(58) Field of Classification Search
USPC .................. 424/93.1; 210/602; 435/257.1
See application file for complete search history.

(56) References Cited

FOREIGN PATENT DOCUMENTS

| DE | 102008023368 A1 | 12/2009 |
|----|-----------------|---------|
| RU | 2192459 C1 | 11/2002 |
| RU | 2263141 C2 | 10/2005 |
| RU | 2350569 C1 | 3/2009 |

OTHER PUBLICATIONS

Search Report issued in connection with PCT/CZ2010/000035 issued by the ISA/EP on Aug. 10, 2010.
Hu, Hanhua, et al., "Alternative Cold Response Modes in *Chlorella* (Chlorophyta, Trebouxiophyceae) from Antarctica", Jan. 2008, Phycologia, vol. 47, No. 1, pp. 28-34.

*Primary Examiner* — Karen Cochrane Carlson
*Assistant Examiner* — Jennifer M Tichy
(74) *Attorney, Agent, or Firm* — Barnes & Thornburg LLP

(57) ABSTRACT

An industrial strain of a unicellular green algae *Parachlorella nurekis* 1904 *KIEG* deposited in the Culture Collection of Algae and Protozoa (CCAP), Scottish Marine Institute, Dunbeg, OBAN, Argyll, PA37 1QA, Scotland, UK, CCAP No. 259/1. A method for eradication of at least one of cyanobacteria, bacteria and fungi comprises treating the at least one of cyanobacteria, bacteria and fungi with an industrial strain of the unicellular green algae *Parachlorella nurekis* 1904 *KIEG* deposited in the Culture Collection of Algae and Protozoa (CCAP), Scottish Marine Institute, Dunbeg, OBAN, Argyll, PA37 1QA, Scotland, UK, CCAP No. 259/1.

6 Claims, 4 Drawing Sheets

PLANKTON STRAIN ALGAE PARACHLORELLA NUREKIS 1904 KIEG AND HIS USE TO EXTERMINATE CYANOBACTERIA, BACTERIA AND FUNGI

CROSS-REFERENCE TO RELATED APPLICATIONS

This application is the U.S. national phase of PCT/CZ2010/000035 filed Mar. 30, 2010. PCT/CZ2010/000035 claims priority to Czech Republic Patent Application Serial No.: PV 2010-157 filed Mar. 4, 2010. The entire disclosures of Czech Republic Patent Application Serial No.: PV 2010-157 and PCT/CZ2010/000035 are hereby incorporated herein by reference.

TECHNICAL FIELDS

The invention refers to the strain of a unicellular green algae *Parachlorella nurekis* 1904 *KIEG* which is designed for biomass production and eradication of cyanobacteria (blue-green algae).

BACKGROUND ARTS

There is a well-known strain of unicellular green algae *Chlorella vulgaris* IFR C-111 characterized by high productivity which meets the requirements of industrial cultivation (patent RU 1751981).

The disadvantage of *Chlorella vulgaris* IFR C-111 lies in the seasonality of its development (during the period from May to December), demand factors of the nutrient medium content, the permanent cycle of the development of cells and the narrow range of cultivation temperatures (26-36° C.).

There is a known strain of unicellular green algae *Chlorella vulgaris* BIN, with a wide range of temperatures acceptable for cultivation (20-40° C.), which is demanding on the substrate, possesses the ability of cleaning sewage waters (patent RU 2192459), and is applied in the biological rehabilitation of water reservoirs (Bogdanov, 2008).

The disadvantage of *Chlorella vulgaris* BIN strain is the absence of seasonal reproduction in natural reservoirs complicating its application in different climatic zones. Poor keeping of vitality in water reservoirs at a temperature range from 0 to 16° C. requires the repeated treatment of the reservoir by the algae. The deficient adaptability to natural conditions of the reservoir requires the additional adaptation of the strain. Another deficiency of *Chlorella vulgaris* BIN is the narrow adaptation range—only to certain sewage waters.

The aim of the invention is to create a new strain of unicellular green algae *Parachlorella nurekis* 1904 *KIEG* which will differ by a higher productivity, seasonal reproduction in natural watersheds and vitality at temperature intervals from 0 to 16° C., and will possess the ability to adapt to natural conditions in different climatic zones, and eradicate cyanobacteria, bacteria and fungi.

DISCLOSURE OF INVENTION

Unicellular green algae are able to eliminate the aforesaid disadvantages of the previous strains. The strain *Parachlorella nurekis* 1904 *KIEG* was cultivated on the basis of *Chlorella vulgaris* BIN from the collection of the Penza Research Agricultural Institute, Russian Academy of Agriculture, This strain was cultivated in natural reservoir water in different climatic zones. As the final result, the transitional strain had been chosen, which is more adaptable and less demanding to the cultivation. Its application demonstrated a high flexibility as regards to water reservoirs of different climatic zones, also the ability to eradicate cyanobacteria, other bacteria and fungi.

Medium: For cultivation of *Parachlorella nurekis* 1904 *KIEG* strain we take per 11 of tap water a nutrient medium containing the following four components.

Nutrient Medium

Component 1: mitric-phosphoric solution—0.3 ml
Component 2: sodium-ferrous solution—0.15 ml
Component 3: copper-cobalt solution—0.2 ml
Component 4: carbon dioxide solution—10 ml Morphological characteristics: New cells have slightly ellipsoidal shape and size of 2-3 μm. Adult vegetative cells have 7-8 μm in diameter. Cells with a diameter of 8-10 μm with already formed autonomic spores are still in the maternal capsule. New cells have thin walls which gradually become thicker. When autonomic spores are released, the (side) is split into 2-3 parts, which remain connected. (Chloroplast wideband and open covers ¾ of cell surface and fits tightly the cell side). Pyrenoid is surrounded by starch paper, consisting of two or three hemispheres. Reproduction is provided by autonomic spores. Spores have the same size. The quantity of spores is four, rarely two and more. The quantity is strictly even. The dividing of cells, genesis and release of autonomic spores runs during the whole day without strict line-up to the fixed hour. Both new and grown-up cells are dark green.

Cultural characteristics: The cells are not accumulated, but distributed equally in the suspension volume. (Vascular) walls are not overgrown. The algae is cultivated and stored in the liquid nutrient medium. It grows well with the application of ammonium nitrate. The algae require the feed of a carbon dioxide solution produced from cellulose.

During cultivation the cells practically do not sediment. In the state of rest the cells start sedimentation in 5-10 days. The process of sedimentation ends in a month period.

The strain's cultivation does not require automatic mixing.

The conditions of cultivation do not (contain) seasonal reproduction. (In natural conditions the seasonality is otherwise very much expressed). In cultivation conditions the strain requires the certain nutrient medium and the maintenance of the biotechnological course of cultivation. In the open-air the algae adapts to the conditions of the watershed which it has been implemented in.

*Parachlorella nurekis* 1904 *KIEG* eliminates bacteria, fungi, implicates decomposition of cells and colony of the cyanobacteria up to their complete elimination.

The strain evolution cycle is unstable; the cells are developed in an asynchronous way.

*Parachlorella nurekis* 1904 *KIEG* strain could be cultivated in 19% salty water.

Algae cultivation does not demand sterility. The strain possesses the ability of creating the monoculture conditions.

Physiological characteristics: The strain is autotrophic; it requires feed of nitrogen, mainly of ammonium nitrate. It grows in the sunlight, also in the conditions of artificial lightning in open reservoirs with lamps. Osram Plantastar 250W. The light penetrates through a layer of 20 cm. The strain has good plankton properties, i.e. ability of uplifting and of equal distribution in cultivation medium.

Living algal cells have negative charges. Loss of charges implicates the coagulation of cells and their agglutination. The ability of sticking to the hydrogenous bubbles is used for extracting the biomass from the cultivation medium by electric flotation.

The optimal temperature for cultivation is 28-30° C. At natural conditions the algae grows in temperature 16-32° C., at the same time it has long vitality in all watersheds at temperatures from 0 to 16° C.

The lighting mode corresponds to the continuation of straight illumination artificial light provided by OSRAM PLANTASTAR 250W lamps—lightning lasts for 10-12 hours. The sufficient minimum of lightning lasts 8-10, maximum 12-14 hours. The strain evolution does not depend on the season or source of light.

The strain behaves antagonistically towards to other water algae, bacteria, fungi or yeast in the cultivation medium. No other algae can be developed in the presence of this strain. Bacteria die and sediment.

The vitality of cells is minimum for 30 years, if the conditions of storage at scattered light and room temperature are kept for the culture.

In natural watersheds the strain kills three kinds of cyanic bacteria (cyanobacteria): *Aphanizomenon, Anabaena* a *Microcystis*. In laboratory conditions *Parachlorella nurekis* 1904 *KIEG* implicates decomposition of cells and colonies of the cyanobacteria up to their complete elimination.

The strain is characterized by high productivity (see the Table) and ability to destroy algal bloom causing cyanobacteria, and other bacteria and fungi.

BRIEF DESCRIPTION OF DRAWINGS

The invention can be better, explained by pictures.

MODE FOR CARRYING OUT THE INVENTION

Example 1

Figure 1:
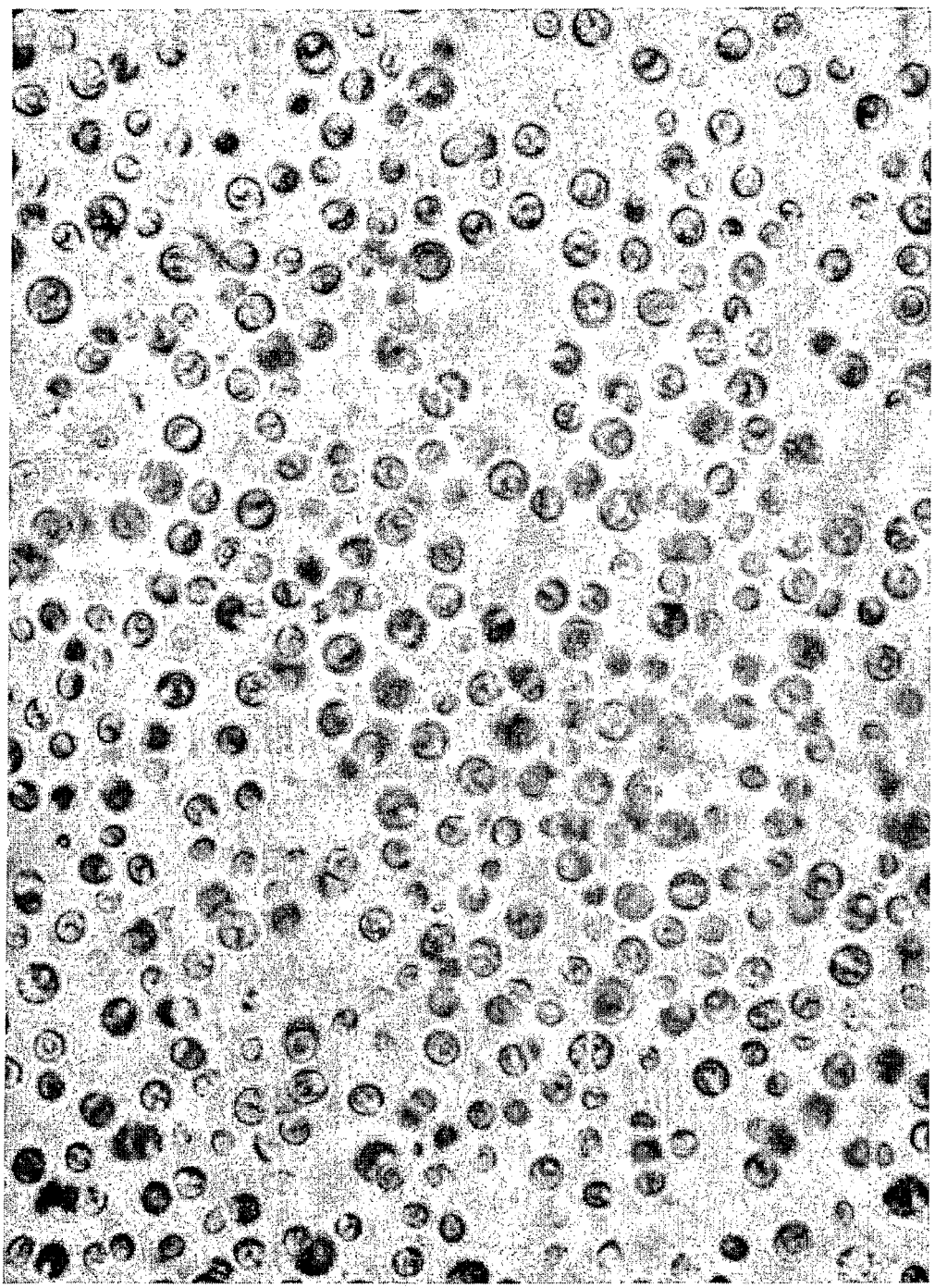
FIG. 1 shows *Chlorella vulgaris* strain by 1000× scale.
Figure 2:
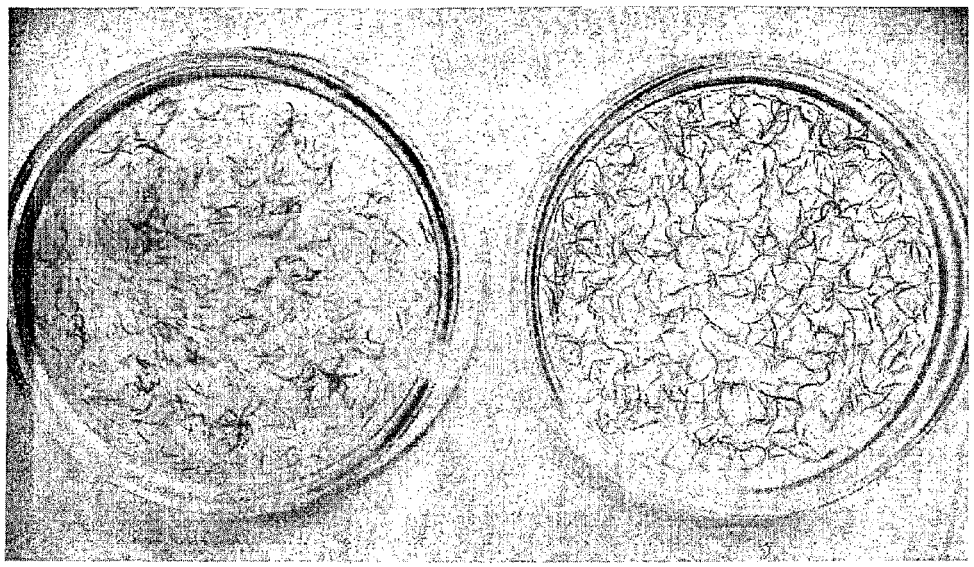
FIG. 2—suppression of Cyanobacteria (*Aphanizomenon flos-aquae*) by *Parachlorella nurekis* 1904 *KIEG* in the beginning of the experiment: 1—experimental, 2—control test-glasses (FIG. 2-6)
Figure 3:
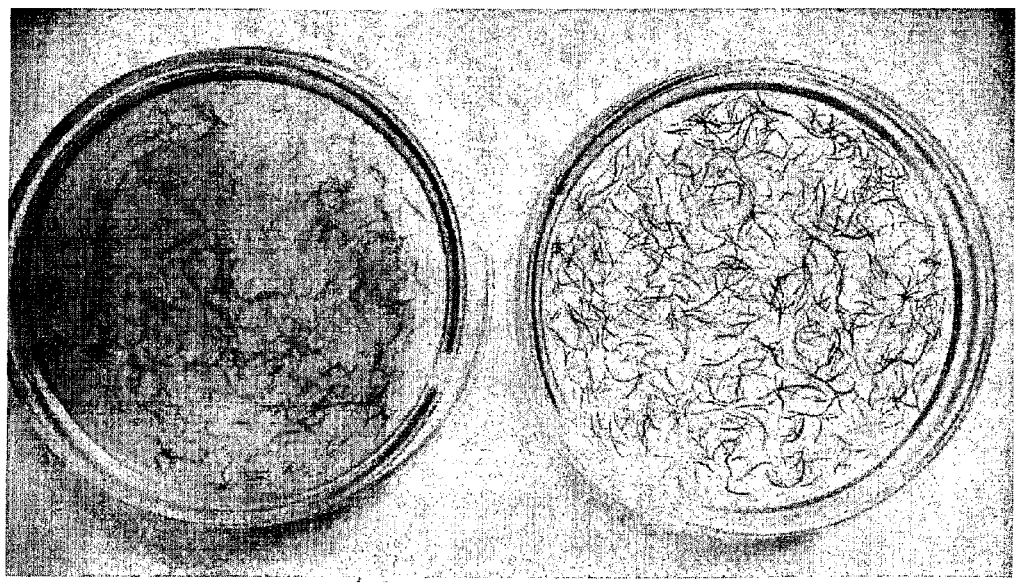
FIG. 3—suppression of Cyanobacteria (*Aphanizomenon flos-aquae*) by *Parachlorella nurekis* 1904 *KIEG* in three hours.
Figure 4:
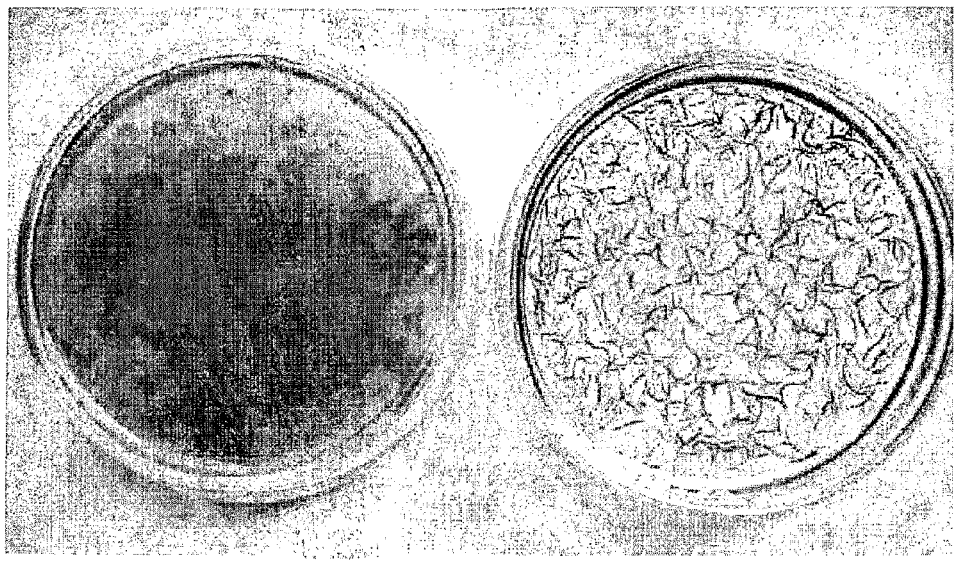
FIG. 4—suppression of Cyanobacteria (*Aphanizomenon flos-aquae*) by *Parachlorella nurekis* 1904 *KIEG* in six hours.
Figure 5:
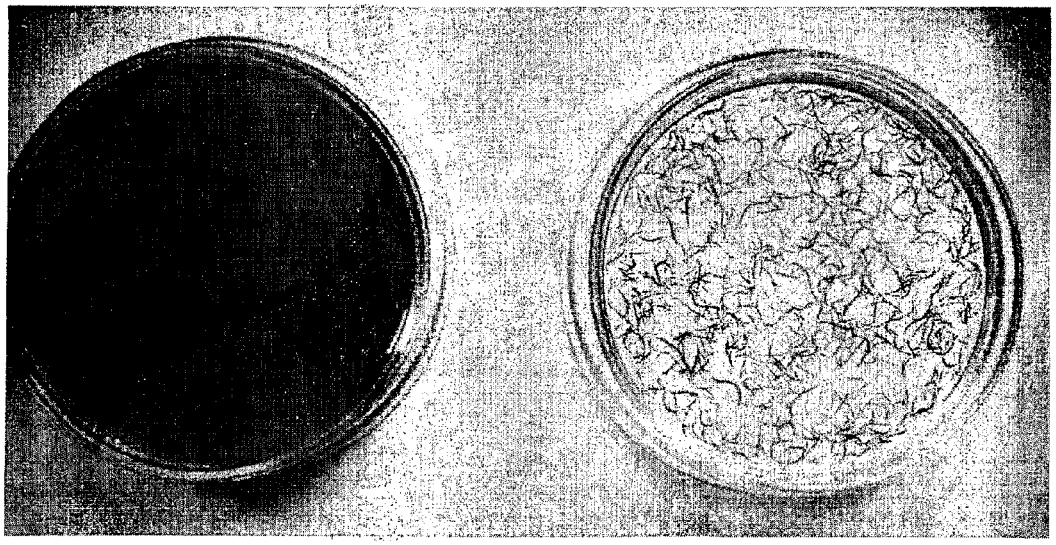
FIG. 5—suppression of cyanobacteria (*Aphanizomenon flos-aquae*) by *Parachlorella nurekis* 1904 *KIEG* in nine hours.
Figure 6:
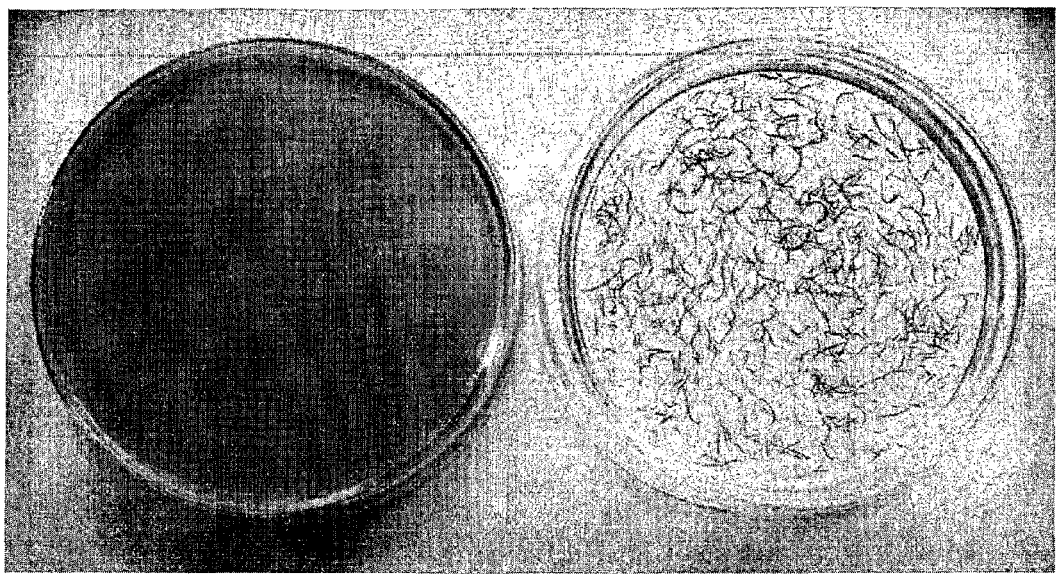
FIG. 6—suppression of Cyanobacteria (*Aphanizomenon flos-aquae*) in twelve hours.

We sample the blooming watershed with *Aphanizomenon flos-aquae* cyanobacteria. 100 ml of the sample is to be filtered, and weighed; biomass is to be extracted (300 mg), and put into the Petri dish, where we then add 100 ml of *Parachlorella* suspension (biomass 60 mg/100 ml). We put 100 ml of the cyanobacteria sample into the second Petri dish. The first Petri dish is an experimental one; the second is the control one. Both dishes should be kept in scattered light and room temperature.

At the beginning of the experiment the colonies of cyanobacteria are well visible in both dishes. In three hours cyanobacteria in the experimental dish darken more, than in the control one. The process of colony decomposition starts in the experimental dish in 6 hours. There are no changes observed in the control dish. In 9 hours cyanobacteria in the experimental dish fully lose their structure. They look as a whole formless unit, darker than cyanobacteria in the control dish. There are no changes observed in the control dish. In 12 hours the experimental dish does not contain visible traces of cyanic bacteria. The control dish shows no changes.

Thus, in 12 hours *Parachlorella* suspension has completely eliminated the colony of cyanobacteria with a biomass 5 times larger than the biomass of *Parachlorella*.

Example 2

We pour 100 ml of water sample from a blooming watershed—*Aphanizomenon flos-aquae* cyanobacteria—into two conical flasks. Biomass of cyanobacteria totals 200 mg/100 ml of water. Then, we add 15 ml of suspension of *Parachlorella nurekis* 1904 *KIEG* into the first flask. The biomass of *Parachlorella* makes 60 mg/100 ml. First flask is an experimental, second is the control one. Both flasks should be kept in scattered light and room temperature (22° C.).

At the beginning of the experiment the colonies of cyanobacteria could be well observed in both flasks. In 6 hours if can be seen that cyanobacteria in the experimental flask darken more than in the control one. Cyanobacteria in the experimental flask completely lose their structure in 12 hours. They look like formless flocks and are darker than cyanobacteria in the control flask. There are no changes observed in the control flask. The experimental flask contains no visible traces of cyanic bacteria in 20 hours.

Within 20 hours the *Parachlorella* suspension implemented to the natural environment of cyanobacteria has completely eliminated the colony of cyanobacteria with a biomass 20 times larger than the biomass of *Parachlorella* itself.

Cyanobacteria were eliminated in the *Parachlorella* medium, as well as after we treated the environment of cyanobacteria with *Parachlorella* suspension. At the same time biomass of cyanobacteria was several times larger than *Parachlorella*'s biomass.

Therefore, the designed algal strain *Parachlorella nurekis* 1904 *KIEG* is more productive against other known strains, and is able to completely eliminate the cyanobacteria causing the algal bloom. For instance, in the result of using this strain at the Tsimlyanskoye watershed (Russia) they managed to entirely destroy cyanobacteria within three years (2006-2009).

TABLE

Comparative indices of efficiency of *Chlorella vulgaris* strains

| | *Chlorella vulgaris* strains | | |
|---|---|---|---|
| Index | IFR C-111 (RU 1751981) | BIN (RU 2192459) | *Parachlorella nurekis* 1904 KIEG (—) |
| Efficiency, dry biomass g/m$^2$ per day | 30 | 60-65 | 70 |
| Optimal temperature of cultivation, ° C. | 26-36 | 20-40 | 28-30 |
| Period of cultivation, months | 12 | 12 | 12 |

INDUSTRIAL APPLICABILITY

*Parachlorella nurekis* 1904 *KIEG* is a strain highly adaptable and undemanding towards the conditions of cultivation. Its utilization has proven high flexibility towards watersheds of various climatic areas and ability to kill cyanobacteria, bacteria and fungi.

A viable sample of the microorganism which is the subject of this application was deposited at an International Depositary Authority Under Article 7 of the Budapest Treaty on the International Recognition of the Deposit of Microorganisms for the Purposes of Patent Procedure. The accession number for the deposit is CCAP 259/1. The date of the deposit was Dec. 15, 2009. The deposited biological material is microalgae. The name and address of the depository is as follows: Scottish Association for Marine Science, Research Services Limited, Culture Collection of Algae and Protozoa (CCAP), Scottish Marine Institute, Dunbeg, Oban, Argyl, PA37 1QA, Scotland.

(a) During the pendency of this application, access to the invention will be afforded to the Commissioner upon request;
(b) all restrictions upon availability to the public will be irrevocably removed upon granting of the patent;
(c) the deposit will be maintained in a public depository for a period of 30 years or 5 years after the last request or for the effective life of the patent, whichever is longer;
(d) a test of the viability of the biological material at the time of deposit will be made (see 37 C.F.R. §1.807); and
(e) the deposit will be replaced if it should ever become inviable.

The invention claimed is:

1. Industrial strain of a unicellular green algae *Parachlorella nurekis* 1904 *KIEG* deposited in the Culture Collection of Algae and Protozoa (CCAP), Scottish Marine Institute, Dunbeg, OBAN, Argyll, PA37 1QA, Scotland, UK, CCAP number 259/1.

2. A method for eradication of at least one of cyanobacteria, bacteria and fungi comprising treating the at least one of cyanobacteria, bacteria and fungi with an industrial strain of a unicellular green algae *Parachlorella nurekis* 1904 *KIEG* deposited in the Culture Collection of Algae and Protozoa (CCAP), Scottish Marine Institute, Dunbeg, OBAN, Argyll, PA371QA, Scotland, UK, CCAP number 259/1.

3. A method for treating at least one of a body of water and a waterway to eradicate at least one of cyanobacteria, bacteria and fungi from said at least one of a body of water and a waterway, said method comprising contacting at least one of cyanobacteria, bacteria and fungi with an industrial strain of a unicellular green algae *Parachlorella nurekis* 1904 *KIEG* deposited in the Culture Collection of Algae and Protozoa (CCAP), Scottish Marine Institute, Dunbeg, OBAN, Argyll, PA371QA, Scotland, UK, CCAP number 259/1.

4. A method of reducing the concentration of at least one of cyanobacteria, bacteria and fungi in at least one of a body of water and a waterway, said method comprising contacting said at least one of a body of water and a waterway with an industrial strain of a unicellular green algae *Parachlorella nurekis* 1904 *KIEG* deposited in the Culture Collection of Algae and Protozoa (CCAP), Scottish Marine Institute, Dunbeg, OBAN, Argyll, PA371QA, Scotland, UK, CCAP number 259/1 under conditions conducive for the growth of *Parachlorella nurekis* 1904 *KIEG*.

5. The method of claim 4 wherein said at least one of a body of water and a waterway is a reservoir.

6. The method of claim 5 wherein said at least one of a body of water and a waterway holds sewage.

* * * * *